United States Patent
Cheng et al.

(12) 
(10) Patent No.: US 6,433,161 B1
(45) Date of Patent: Aug. 13, 2002

(54) GALACTOSYLATED HYDROXYALKYL POLYSACCHARIDES

(75) Inventors: H. N. Cheng, Wilmington; Robert G. Nickol, Hockessin, both of DE (US); George Wang; Jun Li, both of Miami, FL (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 08/841,036

(22) Filed: Apr. 29, 1997

(51) Int. Cl.$^7$ .................. C07B 37/00; C07H 17/04; C07H 1/00; C12P 19/00
(52) U.S. Cl. .................. 536/114; 536/120; 536/123; 536/123.1; 536/124; 514/54; 435/14; 435/72; 435/74
(58) Field of Search .................. 536/120, 114, 536/123.1, 124, 123; 514/54; 435/14, 72, 74

(56) References Cited

U.S. PATENT DOCUMENTS

| 4,435,389 A | 3/1984 | Mutai et al. | 424/181 |
| 4,663,448 A | * 5/1987 | Chiu | 536/111 |
| 4,942,128 A | 7/1990 | Brown, Jr. | 435/101 |
| 4,957,860 A | 9/1990 | Kan et al. | 435/101 |
| 5,149,640 A | 9/1992 | Conishi et al. | 435/100 |
| 5,180,674 A | 1/1993 | Roth | 435/288 |

FOREIGN PATENT DOCUMENTS

| EP | 0281655 A1 | 9/1988 |
| JP | 3157402(91) A | 7/1991 |
| JP | 04279596 | 5/1992 |
| JP | 6329701(94) A | 11/1994 |

OTHER PUBLICATIONS

K. Koizumi et al., "Isolation and Characterization of Novel Heterogeneous Branched Cyclomalto–Oligosaccharides (Cyclodextrins) Produced by Trangalactosylation with α–Galactosidase from Coffee Bean," Carbohydrate Research 278 (1995), pp. 129–142.

* cited by examiner

Primary Examiner—James O. Wilson
Assistant Examiner—Everett White
(74) Attorney, Agent, or Firm—Martin F. Sloan

(57) ABSTRACT

Galactosylated hydroxyalkyl polysaccharides wherein galactose moieties are bound to the hydroxyalkyl polysaccharide by galactosidic bonds, and a process for preparing the galactosylated hydroxyalkyl polysaccharides having the steps: a) providing at least one hydroxyalkyl polysaccharide; and b) treating said hydroxyalkyl polysaccharide with a galactose donor in the presence of galactosidase enzyme for a time sufficient to convert at least a portion of said hydroxyl groups to galactosides.

27 Claims, 3 Drawing Sheets

GALACTOSYLATED HYDROXYALKYL POLYSACCHARIDES

FIELD OF THE INVENTION

This invention relates to galactosylated hydroxyalkyl polysaccharides and methods for preparation thereof.

BACKGROUND OF THE INVENTION

Enzymatic methods for the preparation and modification of polysaccharides are known in the art. For example, U.S. Pat. No. 5,149,640 discloses a galactose transfer product prepared by a process of allowing a microorganism capable of producing a galactose transfer product to act on a combination of lactose or a galactose donor and a galactose receptor; and collecting the galactose transfer product produced.

U.S. Pat. No. 5,180,674 teaches a method and an apparatus for preparing saccharide compositions. The method is reiterative and comprises the following three steps: 1) a glycosyl transferase capable of transferring a preselected saccharide unit to an acceptor moiety is isolated by contacting the acceptor moiety with a mixture suspected of containing the glycosyl transferase under conditions effective to bind the acceptor moiety and glycosyl transferase and thereby isolate the glycosyl transferase. The acceptor moiety is a protein, a glycoprotein, a lipid, a glycolipid or a carbohydrate; 2) the isolated glycosyl transferase is then used to catalyze the bond between the acceptor moiety and the preselected saccharide unit; 3) steps (1) and (2) are repeated a plurality of times with the intermediate product obtained in the first iteration of the method being used as the acceptor moiety of the second iteration.

U.S. Pat. No. 4,957,860 discloses a method for producing oligosaccharides by the reaction between lactose and β-galactosidase.

In U.S. Pat. No. 4,942,128 there is disclosed a method for producing microbial cellulose comprising inoculating a quantity of nutrient medium comprising a polysaccharide derivative such as carboxymethyl cellulose with a cellulose-producing microorganism. Cellulose resulting from this procedure is stated to be highly absorbent.

The preparation of galactosyl cyclodextrin by transgalactosylation has been reported by K. Koizumi et al., *Carbohydrate Research*, 278 (1995) 129–142.

Hydroxyalkyl polysaccharides, particularly hydroxyalkyl cellulose or cellulose derivatives and hydroxyalkyl guar or guar derivatives, are widely used as rheology modifiers, thickening agents and a variety of other applications. Methods to modify these materials by galactosylation, i.e., conversion of hydroxyl groups to galactosides, have been sought in order to modify the properties of the hydroxyalkyl polysaccharides and improve their performance.

SUMMARY OF THE INVENTION

A composition comprises galactosylated hydroxyalkyl polysaccharide wherein the hydroxyalkyl polysaccharide has a degree of substitution by galactose moieties bound to hydroxyl groups of the hydroxyalkyl polysaccharide by galactosidic bonds.

A process for preparing galactosylated hydroxyalkyl polysaccharide comprises:

a) providing at least one hydroxyalkyl polysaccharide; and b) treating said hydroxyalkyl polysaccharide with a galactose donor in the presence of galactosidase enzyme for a time sufficient to cause a degree of substitution by galactose moieties at the hydroxyl groups of the hydroxyalkyl polysaccharide.

DETAILED DESCRIPTION OF THE INVENTION

Figure 1:
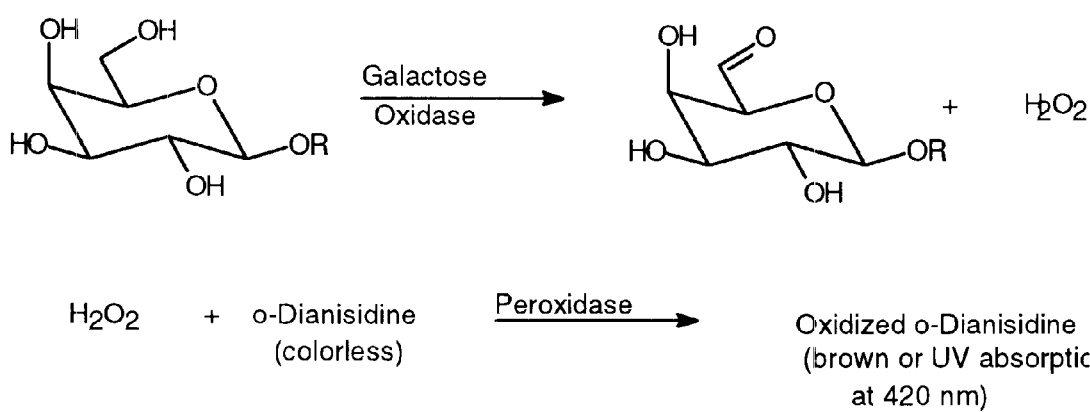
FIG. 1 is a schematic illustration of the method used for determination of bound galactose moieties.

The compositions of this invention comprise galactosylated hydroxyalkyl polysaccharides. A variety of hydroxyalkyl polysaccharides are available commercially. They are readily prepared by methods well known in the art by reaction of polysaccharides, generally under alkaline conditions, with ethylene oxide or $C_1$–$C_{12}$ substituted ethylene oxide.

The hydroxyalkyl polysaccharides for use in this invention include any water-soluble hydroxyalkyl polysaccharide. Preferably they are chosen from the group: hydroxyalkyl cellulose, hydroxyalkyl cellulose ethers, hydroxyalkyl guar, hydroxyalkyl guar derivatives, hydroxyalkyl starch and hydroxyalkyl starch derivatives. Preferably the hydroxyalkyl groups are hydroxyethyl or hydroxypropyl groups. More preferably the hydroxyalkyl groups are hydroxyethyl groups.

Preferred hydroxyalkyl celluloses include hydroxyethyl cellulose (HEC) and hydroxypropyl cellulose (HPC). Hydroxyalkyl cellulose ethers include water soluble ethylhydroxyethyl cellulose (EHEC), carboxymethylhydroxyethyl cellulose (CMHEC), hydroxypropylhydroxyethyl cellulose (HPHEC), methylhydroxypropyl cellulose (MHPC), methylhydroxyethyl cellulose (MHEC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified carboxymethylhydroxyethyl cellulose (HMCMHEC), hydrophobically modified hydroxypropylhydroxyethyl cellulose (HMHPHEC), hydrophobically modified methylhydroxypropyl cellulose (HMMHPC), hydrophobically modified methylhydroxyethyl cellulose (HMMHEC), cationic hydroxyethyl cellulose (cationic HEC) and cationic hydrophobically modified hydroxyethyl cellulose (cationic HMHEC).

Preferred hydroxyalkyl guars include hydroxyethyl guar (HE guar) and hydroxypropyl guar (HP guar). Hydroxyalkyl guar derivatives include carboxymethylhydroxypropyl guar (CMHP guar), hydrophobically modified hydroxyethyl guar (HMHE guar), hydrophobically modified hydroxypropyl guar (HMHP guar), cationic hydrophobically modified hydroxypropyl guar (cationic HMHP guar), and hydrophobically modified carboxymethylhydroxypropyl guar (HMCMHP guar).

Preferred hydroxyalkyl starch derivatives for use in the invention include hydroxyethyl starch, hydroxypropyl starch, hydroxyethyl oxidized starch, hydroxypropyl oxidized starch, hydroxyethyl cationic starch, hydroxypropyl cationic starch, hydroxyethyl starch acetate, hydroxypropyl starch acetate, hydroxyethyl starch phosphate, hydroxypropyl starch phosphate, hydroxyethyl depolymerized starch and hydroxypropyl depolymerized starch.

More preferred hydroxyalkyl polysaccharides for use in the invention are hydroxyethyl cellulose (HEC), ethylhydroxyethyl cellulose (EHEC), carboxymethylhydroxyethyl cellulose, methylhydroxyethyl cellulose (MHEC), hydrophobically modified hydroxyethyl cellulose (HMHEC), hydrophobically modified ethylhydroxyethyl cellulose (IMEHEC), hydrophobically modified carboxymethylhydroxyethyl cellulose (HMCMHEC), hydrophobically modified methylhydroxyethyl cellulose (HMMHEC), cationic hydroxyethyl cellulose (cationic HEC) and cationic hydrophobically modified hydroxyethyl cellulose (cationic HMHEC).

The most preferred hydroxyalkyl polysaccharide is hydroxyethyl cellulose (HEC).

The galactosylation reaction is carried out in the presence of a galactose donor and galactosidase enzyme. Suitable galactose donors include galactose itself and any di- oligo- or polysaccharide which can yield galactose on hydrolysis. Preferably the galactose donor is one of the group lactose, galactose, galactomannans, and nitrophenyl, dinitrophenyl, and trinitrophenyl glycosides thereof. Preferred donors include lactose and galactose. The most preferred donor is lactose.

The galactosidase enzymes for use in galactosylation reaction are preferably β-galactosidases. The galactosylation reaction may be carried out in the presence of any microorganism that produces β-galactosidase. Specific examples of such microorganisms are *Bacillus circulans, Aspergillus oryzae* and *E. coli*.

For culturing of these or other microorganisms used for the galactosylation reaction, any nutrient source is usable so long as it can be assimilated by the microorganism. The culture is supplemented with the appropriate hydroxyalkyl polysaccharide and galactose donor at the initial stage of culturing or during the culturing. Alternatively, the galactosylated product may be produced using resting cultures.

A method using resting cultures simply employs a culture solution as is. Another method comprises isolating cells by centrifugation, or an equivalent technique, resuspending the cells in phosphate buffer or equivalent, further adding galactose donor and hydroxyalkyl polysaccharide to the suspension, and then allowing these ingredients to react. The microorganisms may be viable cells, or the cells may have been subjected to treatment with acetone or may have been subjected to freeze drying. The microorganism may also have been immobilized on a carrier or may have been used in a bioreactor utilizing an ultrafiltration membrane.

A preferred method for carrying out the reaction is under cell-free condition, i.e., utilizing enzyme isolated from the appropriate microorganism, together with hydroxyalkyl polysaccharide and galactose donor. In this case the preferred enzymes are those β-galactosidases isolated from the organisms *Bacillus circulans, Aspergillus oryzae* and *E. coli*.

In the preferred cell-free method the reaction is carried out in aqueous solution. Water-miscible organic cosolvents may be utilized in levels that do not destroy the activity of the enzyme. The optimum pH of the reaction medium depends on the source of the enzyme utilized, but is preferably in the range. of from about 4 to about 9.5, more preferably from about 4.5 to about 7. The pH can be maintained by inclusion of appropriate buffering materials, e.g., sodium acetate.

The level of hydroxyalkyl polysaccharide in the reaction medium is not critical, the process being operable at any level of dissolved hydroxyalkyl polysaccharide. Preferably the level will be in the range of from about 0.1 weight percent to about 50 weight percent, more preferably from about 0.5 to about 15 weight percent, and most preferably from about 1 to about 10 weight percent.

The ratio of galactose donor to hydroxyalkyl polysaccharide on a weight basis can vary over a wide range. Generally it is found that the higher the ratio, the higher the level of galactosylation that can be achieved. The maximum ratio of galactose donor to hydroxyalkyl polysaccharide is limited only by the solubility of the donor in the reaction medium. In the work disclosed here, ratios of from about 1:1 to about 100:1 have been found satisfactory. However, ratios beyond those limits are within the bounds of the invention as well.

The amount of galactosidase used is not critical. Even very small amounts will allow the reaction to proceed, albeit at a low rate. Preferably the amount of galactosidase is from about 0.5 to about 1,000 units per gram of hydroxyalkyl polysaccharide. More preferably, the amount is from about 5 to about 500 units, and most preferably from about 10 to about 150 units per gram of hydroxyalkyl polysaccharide. A "unit" of galactosidase enzyme is defined as the amount that will hydrolyze 1 micromole per minute of p-nitrophenyl-α-D-galactoside to p-nitrophenol and galactose at pH 6.5 and 25° C.

The temperature for reaction is preferably from about room temperature, i.e., about 20°–25° C., up to a temperature where the enzyme becomes inactivated, about 85° C. Temperatures lower than room temperature may be utilized, but with a concomitant increase in reaction time.

The reaction time for optimum galactosylation depends on a variety of factors, e.g., temperature, concentrations of the reactants, and the structures of the hydroxyalkylated polysaccharide and galactose donor that are chosen for reaction. Furthermore, there can be a competing reaction of enzymatic hydrolysis, which results in loss of bound galactose groups. For this reason, some experimentation may be necessary to determine the optimum time for a specific set of reaction conditions. Those skilled in the art of enzyme reactions are able to determine the optimum time without undue experimentation.

The course of the reaction may be conveniently followed by enzymatic assay utilizing galactose oxidase as shown in FIG. 1, where R represents the hydroxyalkylated polysaccharide residue. The oxidation reaction with galactose oxidase is highly specific for galactose and galactosides. The oxidation reaction catalyzed by galactose oxidase can be followed by determination of the simultaneously produced hydrogen peroxide by a peroxidase-chromogen test in a UV spectrophotometer at 420 nm, or by visual observation of color. The hydrogen peroxide is determined by measuring its reaction with peroxidase in the presence of a suitable chromogenic oxygen acceptor such as o-toluidine or o-dianisidine.

Prior to the analysis the product must be treated to remove unreacted galactose and/or galactose donor. One convenient treatment method is dialysis, with a molecular weight cutoff of about 8,000, which allows separation of the lower molecular weight galactose and/or galactose donor from galactosylated hydroxyalkyl polysaccharide, unreacted hydroxyalkyl polysaccharide and enzyme. The same effect, i.e., rough separation of small molecules from macromolecules, can be accomplished by gel filtration by Sepharose CL-4B gels, which can fractionate polymers with a molecular weight range of from about 10,000 to about $4 \times 10^7$.

The level of galactosylation in the galactosylated hydroxyalkyl polysaccharides is expressed as "degree of substitution." Polysaccharides generally contain 3 reactive hydroxyl groups per monomer unit. Hydroxyalkylation of the polysaccharide does not change the number of these hydroxyl groups. Instead, it replaces original hydroxyl groups with hydroxyl groups that are at the end of hydroxyalkyl chains. The average number of hydroxyl groups per monomer unit substituted by galactose moieties is the degree of substitution. Theoretically then, the maximum degree of substitution is 3. In the present invention the degree of substitution is from about 0.01 to about 3. Preferably it is from about 0.01 to about 1, and more preferably from about 0.01 to about 0.5.

Figure 2:
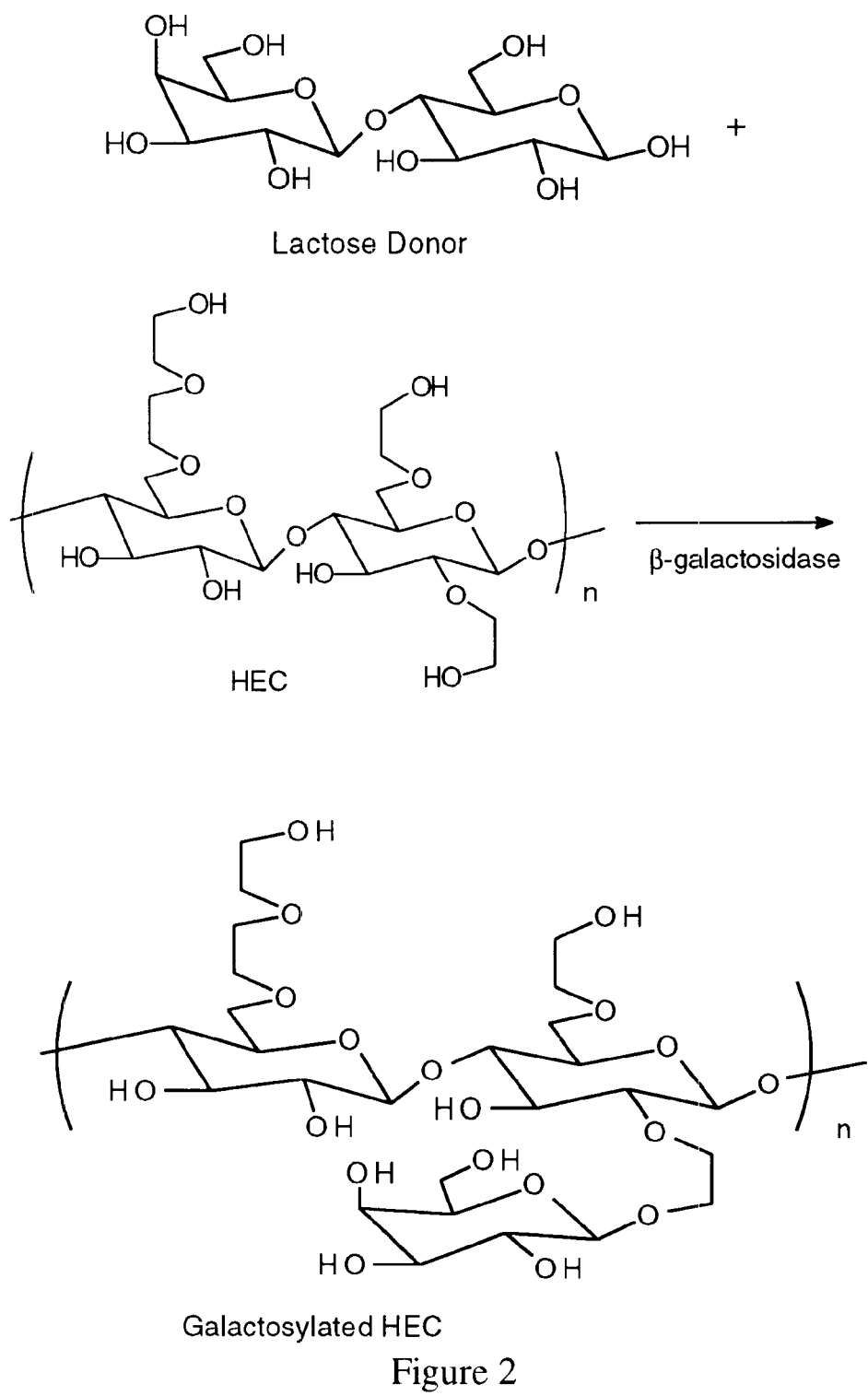
FIG. 2 illustrates the reaction of hydroxyethyl cellulose (HEC) with a lactose donor.

With regard to the mechanism of the galactosylation reaction and the structure of the products, the following remarks, while believed to be correct, are speculative and should not be construed as limiting the invention. Polysaccharides generally contain hydroxyl groups in great numbers along the polymer backbone. As indicated above, hydroxyalkylation of the polysaccharide does not change the number of these hydroxyl groups. Instead, it replaces original hydroxyl groups with hydroxyl groups that are at the end of the hydroxyalkyl chains. It is believed that the galactosylation process of this invention favors reaction at these hydroxyalkyl hydroxyls. In particular, when the hydroxyalkyl polysaccharide is a hydroxyethyl polysaccharide, the hydroxyalkyl hydroxyls are primary and are expected to be greatly favored for reaction over the large number of secondary hydroxyl groups present on the backbone of a typical polysaccharide. An illustration of the proposed reaction, using hydroxyethyl cellulose (HEC) as an example, is in FIG. 2.

The galactosylated hydroxyalkyl polysaccharides of this invention have utility in a variety of areas including thickening agents, rheology modifiers, and protective colloids.

This invention is illustrated by the following examples, which are exemplary only and not intended to be limiting. All percentages, parts, etc., are by weight unless otherwise indicated.

Materials
Hydroxyethyl cellulose: Natrosol®250LR, from Hercules Incorporated, Wilmington, Del.
Hydroxypropyl cellulose: Klucel Type MF, from Hercules Incorporated, Wilmington, Del.
Galactosidases: β-Galactosidases from *Aspergillus oryzae* (EC 3.2.1.23; Grade XI) and from *E. coli.* (EC 3.2.1.23; Grade VI) were purchased from Sigma Inc., St. Louis, Mo. β-Galactosidase from *Bacillus circulans* was obtained from Daiwai Kasei Co. Ltd., Osaka, Japan.
CLONEZYME Thermostable Glycosidases library was obtained from Recombinant Biocatalysis, Inc., Philadelphia, Pa.

Method for Enzymatic Galactosylation and Polymer Purification
To a solution of hydroxyalkyl polysaccharide and lactose in sodium acetate buffer (pH 4.85) was added β-galactosidase. After the desired reaction time, the reaction mixture was quenched by heating for 5 minutes at 100° C. The reaction mixture was then directly loaded onto a Sepharose CL-4B gel column, which was then eluted with water. The fractions containing polymer (determined by thin layer chromatography on silica gel using 3:7:2 ammonia:i-propanol:water) were lyophilized to result in white membrane-like solid.

Method for the Peroxidase-Chromogen Test
The oxidase-chromogen reagent was prepared by mixing 0.5 ml of galactose oxidase (70 units), 0.5 ml of horseradish peroxidase (100 mg/l), 0.5 ml of o-toluidine (200 mg/l) and 0.5 ml of the substrate solution (the reaction concentration was less than $1.39 \times 10^{-4}$ M, i.e., 278 mmoles in 2 ml of solution), and then placing the mixture in an incubator at 30° C. for 1 hour. Maximum chromogenesis took place within 60 minutes. The color that developed was read at 420 nm. To calibrate the test, a plot of absorbance at 420 nm versus known amounts of lactose was prepared. Comparison of the test results with the calibration plot gave values for the amount of bound galactose in the test materials.

EXAMPLE 1

This example illustrates the effect of reaction time on the extent of galactosylation of hydroxyethyl cellulose under a standard set of reaction conditions.

Figure 3:
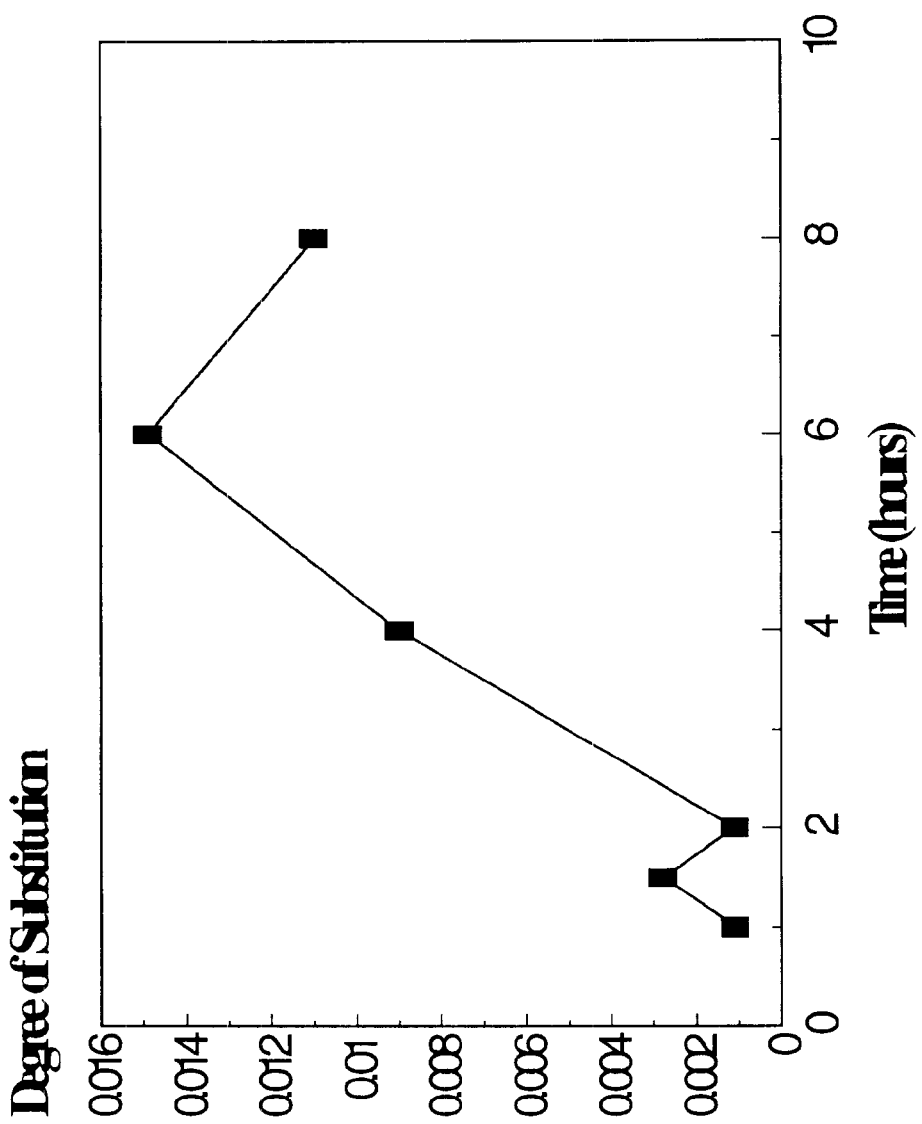
FIG. 3 is a graph of degree of substitution of hydroxyethyl cellulose by galactose moieties at varying reaction times.

Lactose (2 g), hydroxyethyl cellulose (0.219 g) and *Aspergillus oryzae* source β-galactosidase (0.025 g, 110 units) were dissolved in 2.5 ml of sodium acetate buffer at pH 4.5. The reaction was allowed to proceed at room temperature and monitored to determine the extent of galactosylation at time intervals using the standard test method. The results are presented below in FIG. 3.

It is apparent that the highest level of galactosylation occurred at about 6 hours. The drop off at times greater than 6 hours is believed to be due to enzymatic hydrolysis of the product.

EXAMPLE 2

This example demonstrates the weak glucosidase activity of *Aspergillus oryzae* β-galactosidase.

Two reactions were compared as follows. In the first, a 9% by weight solution of hydroxyethyl cellulose in sodium acetate buffer at pH 4.5 was used as a blank, while in the second, a 9% by weight solution of hydroxyethyl cellulose in the same buffer was incubated with β-galactosidase (10 mg/ml, 44 units/ml). Both reactions were allowed to proceed for 6 hours and then quenched by boiling for 10 minutes. The intrinsic viscosities of both reaction mixtures were determined at 25° C. using a Ubbelohde viscometer. In the first, the intrinsic viscosity was 1.4, and in the second 0.55. This demonstrates a depolymerization effect in the galactosylation using *Aspergillus oryzae* β-galactosidase.

EXAMPLE 3

This example demonstrates the effects of varying ratios and concentration of galactose donor and hydroxyethyl cellulose acceptor, and the effect on the reaction of the presence of organic solvent.

Reactions utilizing enzyme from *Aspergillus oryzae* were carried out at room temperature in buffer at pH 4.85, and the enzyme was used at a level of 25 mg (110 units) in 2.5 ml of reaction medium. The reactions utilizing CLONEZYME Gly001-02 were carried out at 70° C. in buffer at pH 6.0. The CLONEZYME Gly001-02 was used at a level of 1 mg in 2.5 ml of reaction medium. The results are presented in Table 1.

It is clear that organic solvents inhibit, but do not completely suppress the enzyme activity, and that increasing the ratio of galactose donor to hydroxyethyl cellulose increases the level of galactosylation.

TABLE 1

Galactosylation of Hydroxyethyl Cellulose

| Enzyme Source | HEC, wt. % | Lactose, wt. % | Organic Solvent | Reaction Time (hrs.) | Degree of Substitution |
| --- | --- | --- | --- | --- | --- |
| *Aspergillus oryzae* | 4 | 17 | — | 6 | 0.006 |
| *Aspergillus oryzae* | 4 | 34 | — | 6 | 0.012 |
| *Aspergillus oryzae* | 4 | 68 | — | 6 | 0.012 |
| *Aspergillus oryzae* | 7 | 17 | — | 6 | 0.006 |
| *Aspergillus oryzae* | 7 | 34 | — | 6 | 0.012 |
| *Aspergillus oryzae* | 7 | 68 | — | 6 | 0.006 |
| *Aspergillus oryzae* | 0.7 | 34 | — | 6 | 0.024 |
| *Aspergillus oryzae* | 0.7 | 34 | DMSO[1] | 6 | 0.009 |
| *Aspergillus oryzae* | 0.7 | 34 | $CH_3CN$[1] | 6 | 0.012 |
| *Aspergillus oryzae* | 0.7 | 34 | — | 48 | 0.033 |
| *Aspergillus oryzae* | 0.4 | 34 | — | 48 | 0.030 |
| CLONEZYME[2] | 9 | 82 | — | 6 | 0.028 |
| CLONEZYME[2] | 9 | 82 | $CH_3CN$[1] | 6 | 0.012 |
| CLONEZYME[2] | 7 | 82 | — | 48 | 0.018 |
| CLONEZYME[2] | 0.7 | 34 | — | 48 | 0.009 |

[1]DMSO = dimethyl sulfoxide, $CH_3CN$ = acetonitrile. Both were used at a 1/1 ratio with the aqueous buffer system.
[2]CLONEZYME Gly001-02

EXAMPLE 4

This example describes a method for increasing the level of galactosylation by recycling product through several reaction stages.

Galactosylation was carried out for 6 hours using the same conditions described for Example 1. Product was isolated by dialysis and lyophilization in the usual way. The degree of substitution was 0.036. The product was recycled through the same reaction conditions two more times. Degrees of substitution of 0.069 and 0.048 were found in the products of the first recycle and second recycle respectively.

EXAMPLE 5

This example illustrates the galactosylation of hydroxypropyl cellulose in the presence of β-galactosidase.

Two experiments were carried out. In the first, the enzyme *Aspergillus oryzae* (0.1 g, 440 units), hydroxypropyl cellulose (0.1 g) and lactose (4.6 g) were dissolved in 13.3 ml of sodium acetate buffer (pH 4.85). After 48 hours at room temperature, the reaction was quenched by heating for 5 minutes at 100° C. It was then directly loaded onto a Sepharose CL-4B column and eluted with water. The fractions containing the polymer (determined by thin layer chromatography on silica gel using $NH_3$/:i-propyl alcohol/water, 3:7:2) were lyophilized to yield the desired product. The degree of substitution was 0.027.

In the second experiment, the procedures and amounts of enzyme, hydroxypropylcellulose and lactose were the same, but they were dissolved in 13.3 ml of a 1/1 mixture of acetonitrile and sodium acetate buffer. The degree of substitution was 0.024.

It is not intended that the examples presented here should be construed to limit the invention, but rather they are submitted to illustrate some of the specific embodiments of the invention. Various modifications and variations of the present invention can be made without departing from the scope of the appended claims.

What is claimed is:

1. A compound comprising galactosylated hydroxyalkyl polysaccharide wherein the galactosylated hydroxyalkyl polysaccharide contains galactose moieties bound to the oxygen atom of the hydroxyl groups of the hydroxyalkyl polysaccharide by galactosidic bonds, and wherein the hydroxyalkyl polysaccharide is selected from the group consisting of hydroxyethyl cellulose, hydroxypropyl cellulose, water soluble ethylhydroxyethyl cellulose, carboxymethylhydroxyethyl cellulose, hydroxypropylhydroxylethyl cellulose, methylhydroxypropyl cellulose, methylhydroxyethyl cellulose, hydrophobically modified hydroxyethyl cellulose, hydrophobically modified hydroxypropyl cellulose, hydrophobically modified ethylhydroxyethyl cellulose, hydrophobically modified carboxymethylhydroxyethyl cellulose, hydrophobically modified hydroxypropylhydroxyethyl cellulose, hydrophobically modified methylhydroxypropyl cellulose, hydrophobically modified methylhydroxyethyl cellulose, cationic hydroxyethyl cellulose, cationic hydrophobically modified hydroxyethyl cellulose, hydroxyethyl guar, hydroxypropyl guar, carboxymethylhydroxypropyl guar, hydrophobically modified hydroxyethyl guar, hydrophobically modified hydroxypropyl guar, and hydrophobically modified carboxymethylhydroxypropyl guar.

2. The compound of claim 1 wherein the hydroxyalkyl polysaccharide is selected from the group consisting of hydroxyethyl cellulose, hydroxypropyl cellulose, water soluble ethylhydroxyethyl cellulose, carboxymethylhydroxyethyl cellulose, hydroxypropylhydroxylethyl cellulose, methylhydroxypropyl cellulose, and methylhydroxyethyl cellulose.

3. The compound of claim 1 wherein the hydroxyalkyl polysaccharide is selected from the group consisting of hydroxyethyl cellulose and hydroxypropyl cellulose.

4. The compound of claim 1 wherein the hydroxyalkyl polysaccharide is hydroxyethyl cellulose.

5. The compound of claim 1 wherein the degree of substitution of hydroxyalkyl polysaccharide by galactose moieties is from about 0.01 to about 3.

6. The compound of claim 1 wherein the degree of substitution by galactose moieties is from about 0.01 to about 1.

7. The compound of claim 1 wherein the degree of substitution by galactose moieties is from about 0.01 to about 0.5.

8. The compound of claim 1 wherein the hydroxyalkyl polysaccharide is hydroxyethyl cellulose and the degree of substitution of hydroxyalkyl polysaccharide by galactose moieties is from about 0.01 to about 3.

9. The compound of claim 1 wherein at least a portion of the galactose moieties are bound to the oxygen atom of the hydroxyl groups at the end of the hydroxyalkyl chains of the hydroxyalkyl polysaccharide.

10. A process for preparing the galactosylated hydroxyalkyl polysaccharide of claim 1 comprising:
  a) providing at least one hydroxyalkyl polysaccharide; and
  b) treating said hydroxyalkyl polysaccharide with a galactose donor in the presence of galactosidase enzyme for a time sufficient to effect galactosylation of at least a portion of the hydroxyl groups of the hydroxyalkyl polysaccharide.

11. The process of claim 10 wherein the hydroxyalkyl polysaccharide is selected from the group consisting of hydroxyethyl cellulose, hydroxyethyl guar, hydroxyethyl guar derivatives, hydroxypropyl cellulose, hydroxypropyl guar and hydroxypropyl guar derivatives.

12. The process of claim 10 wherein the hydroxyalkyl polysaccharide is selected from the group consisting of consisting of hydroxyethyl cellulose, hydroxypropyl cellulose, water soluble ethylhydroxyethyl cellulose, carboxymethylhydroxyethyl cellulose, hydroxypropylhydroxyethyl cellulose, methylhydroxypropyl cellulose, methylhydroxyethyl cellulose, hydrophobically modified hydroxyethyl cellulose, hydrophobically modified hydroxypropyl cellulose, hydrophobically modified ethylhydroxyethyl cellulose, hydrophobically modified carboxymethylhydroxyethyl cellulose, hydrophobically modified hydroxypropylhydroxyethyl cellulose, hydrophobically modified methylhydroxypropyl cellulose, hydrophobically modified methylhydroxyethyl cellulose (HMMHEC), cationic hydroxyethyl cellulose and cationic hydrophobically modified hydroxyethyl cellulose.

13. The process of claim 10 wherein the hydroxyalkyl polysaccharide is selected from the group consisting of hydroxyethyl guar, hydroxypropyl guar, carboxymethylhydroxypropyl guar, hydrophobically modified hydroxyethyl guar, hydrophobically modified hydroxypropyl guar, cationic hydrophobically modified hydroxypropyl guar, and hydrophobically modified carboxymethylhydroxypropyl guar.

14. The process of claim 10 wherein the hydroxyalkyl polysaccharide is hydroxyethyl cellulose.

15. The process of claim 10 wherein the hydroxyalkyl polysaccharide is hydroxypropyl cellulose.

16. The process of claim 10 wherein the galactose donor is selected from the group consisting of lactose, galactose, galactomannans and nitrophenyl, dinitrophenyl, and trinitrophenyl glycosides thereof.

17. The process of claim 10 wherein the galactose donor is a galactomannan selected from the group consisting of guar and locust bean gum.

18. The process of claim 10 wherein the galactosidase enzyme is a $\beta$-galactosidase isolated from a microorganism selected from the group consisting of *Bacillus circulans, Aspergillus oryzae* and *E. coli*.

19. The process of claim 18 wherein the galactosidase enzyme is a $\beta$-galactosidase isolated from *Aspergillus oryzae*.

20. The process of claim 10 that takes place in aqueous medium.

21. The process of claim 20 wherein the aqueous medium contains water-miscible organic solvent.

22. The process of claim 10 wherein the ratio of galactose donor to hydroxyalkyl polysaccharide on a weight basis is from about 1:1 to about 100:1.

23. The process of claim 10 wherein the galactosidase enzyme is used at a level of from about 0.5 to about 1,000 units per gram of hydroxyalkyl polysaccharide.

24. The process of claim 23 wherein the galactosidase enzyme is used at a level of from about 5 to about 500 units per gram of hydroxyalkyl polysaccharide.

25. The process of claim 24 wherein the galactosidase enzyme is used at a level of from about 10 to about 150 units pet gram of hydroxyalkyl polysaccharide.

26. The process of claim 10 wherein the galactose donor is selected from the group consisting of lactose, galactose, galactomannans and nitrophenyl, dinitrophenyl, and trinitrophenyl glycosides thereof, and the galactosidase enzyme is a $\beta$-galactosidase isolated from a microorganism selected from the group consisting of *Bacillus circulans, Aspergillus oryzae* and *E coli*.

27. The process of claim 26 wherein the ratio of galactose donor to hydroxyalkyl polysaccharide is from about 1:1 to about 100:1 and the galactosidase enzyme is used at a level of from about 0.5 to about 1,000 units per gram of hydroxyalkyl polysaccharide.

* * * * *